United States Patent [19]

Bier et al.

[11] Patent Number: 4,897,169
[45] Date of Patent: Jan. 30, 1990

[54] PROCESS AND APPARATUS FOR RECYCLING ISOELECTRIC FOCUSING AND ISOTACHOPHORESIS

[76] Inventors: Milan Bier, 5341 E. 7th St., Tucson, Ariz. 85711; Garland E. Twitty, 8340 E. Lee St., Tucson, Ariz. 85715

[21] Appl. No.: 333,867

[22] Filed: Apr. 3, 1989

Related U.S. Application Data

[63] Continuation of Ser. No. 897,748, Aug. 18, 1986.

[51] Int. Cl.$^4$ .................. G01N 27/28; G01N 27/26
[52] U.S. Cl. .................. 204/183.2; 204/183.3; 204/299 R
[58] Field of Search .............. 204/299 R, 183.2, 183.3

[56] References Cited

U.S. PATENT DOCUMENTS

| | | | |
|---|---|---|---|
| 3,149,060 | 9/1964 | Dorby et al. | 204/183.3 |
| 3,498,905 | 3/1970 | Strickler | 204/183.3 X |
| 3,519,549 | 7/1970 | Grassmann et al. | 204/299 R |
| 4,204,929 | 5/1980 | Bier | 204/299 R |
| 4,349,429 | 9/1982 | Rhodes et al. | 204/299 R |
| 4,362,612 | 12/1982 | Bier | 204/299 R |

FOREIGN PATENT DOCUMENTS 59-052743 3/1984 Japan ................ 204/299 R

OTHER PUBLICATIONS

Cornelius F. Ivory et al., "Scale-Up of the Free Flow Electrophoresis Device", Electrophoresis, 83 (1983).

Primary Examiner—John F. Niebling
Assistant Examiner—John S. Starsiak, Jr.
Attorney, Agent, or Firm—Kenyon & Kenyon

[57] ABSTRACT

The disclosure is directed to a process and apparatus for isoelectric focusing and isotachophoresis of fluids. Recycling of the process fluid is established in a first direction through an electrophoretic chamber having parallel walls, the electric field being applied in a second direction. Externally of the chamber, the flow of fluid is subdivided into a plurality of closed loops, cooled to dissipate the Joule heat. While maintaining conditions of laminar flow within the chamber, unusual fluid stabilization against convective, electroosmotic and other fluid flow disturbances is obtained if the gap between the parallel walls of the chamber is kept narrow and the fluid flow is rapid, to maximize shear stress at the walls of the chamber and minimize the fluid residence time in the chamber.

17 Claims, 3 Drawing Sheets

PROCESS AND APPARATUS FOR RECYCLING ISOELECTRIC FOCUSING AND ISOTACHOPHORESIS

"This is a continuation of co-pending application Ser. No. 897,748 filed on Aug. 18, 1986."

BACKGROUND OF THE INVENTION

The invention relates to techniques for the separation, purification, or both, of biolgical materials and, more specifically, to a method and apparatus for isoelectric focusing and isotachophoresis.

Isoelectric focusing, isotachophoresis, and zone electrophoresis are variants of electrophoretic techniques, differing in the buffer system employed and mode of separation achieved. The theoretical distinction of three methods has been described in some detail in Bier, 219 Science 1281-87 (1983).

Zone Electrophoresis ("ZE"), is the oldest of these techniques and most commonly used. Separation is carried out in the presence of a background of homogeneous buffer, and sample components separate according to their mobilities in this buffer. No steady state is ever reached, but migration continues with gradual broadening of sample zones due to diffusion and other effects.

Isotachophoresis ("ITP") is a more recent variant of electrophoresis, characterized by the fact that separation is carried out in a discontinuous buffer system. Sample material to be separated is inserted between a "leading electrolyte" and a "terminating electrolyte", the characteristic of these two buffers being that the leader has to have ions of net mobility higher than those of sample ions, while the terminator must have ions of net mobilities lower than those of sample ions. In such a system, sample components sort themselves according to decreasing mobilities from leader to terminator, in a complex pattern governed by the so-called Kohlrausch regulating function. The process has been described repeatedly, as for instance, Bier and Allgyer, Electrokinetic Separation Methods 443-69 (Elsevier/North-Holland 1979).

It is further characteristic of ITP that a steady state is eventually reached, where all components migrate at same velocity (hence the name) in sharply defined contiguous zones. Sample components can be separated in such a contiguous train of components by insertion of "spacers" with mobilities intermediary between those of the components one wishes to separate.

Isoelectric focusing ("IEF"), also sometimes called electrofocusing, is a powerful variant of electrophoresis. The principle of IEF is based on the fact that proteins and peptides, as well as most biomaterials, are amphoteric in nature, i.e., are positively charge in acid media and negatively charged in basic media. At a particular pH value, called the isoelectric point (PI), there is reversal of net charge polarity, the biomaterials acquiring zero net charge.

If such amphoteric materials are exposed to a d.c. current of proper polarity in a medium exhibiting a pH gradient, they will migrate, i.e., 'focus' toward the pH region of their PI, where they become virtually immobilized. Thus a stationary steady state is generated, where all components of the mixture have focused to their respective PIs.

The pH gradient is mostly generated 'naturally' i.e, through the electric current itself. Appropriate buffer systems have been developed for this purpose, containing amphoteric components which themselves focus to their respective PI values, thereby buffering the pH of the medium.

Such buffer mixtures are known as 'carrier ampholytes', the best known being "Ampholine", a trademark of the LKB Produkter AB, a Swedish company. Other carrier ampholyte mixtures can be formulated by judicious mixing of suitable ampholytes, as, for example, described in Bier, 211 J. Chromatography 313-35 (1981).

The two variants, IEF and ITP, differ in that IEF attains a stationary steady state whereas in ITP a migrating steady state is obtained. Thus, in IEF a finite length of migrating channel is always sufficient. In ITP, complete resolution may require longer migrating channels than is practical. In such case, the migrating components can be virtually immobilized by applying a counterflow of leading electrolyte, the rate of counterflow being matched to the rate of frontal migration of the sample ions. This is also known in the art.

IEF is most frequently carried out in polyacrylamide or agarose gels, where all fluid flow disturbances are minimized. ITP is most often carried out in capillaries. The sample is inserted at one end of the capillary, at the interface between leader and terminator, and the migration of separated components recorded by appropriate sensors at the other end of the capillary. Both such systems are used mainly for analytical or micro-preparative purposes.

The scaling up of any electrophoretic technique is difficult because of the need to stabilize the fluid system against convection. The easiest fluid stabilization is achieved in gels or with other supporting media, such as granulated beds, etc. Unfortunately, such stabilized systems do not lend themselves to separations involving flow of process fluid, yet such flow, whether continuous or recycling, appears to be the best approach for increasing the capacity of the techniques. Continuous flow is best carried out in free fluids, unsupported by gels or granulated beds. Separations in free fluids require stabilization against flow disturbances. These disturbances could disrupt the orderly separation of sample components. The need for fluid stabilization is well recognized by practitioners of the art and, to achieve it, a variety of principles have been utilized and incorporated into diverse instruments.

One of the most common principles utilized for flow stabilization is confinement of the process fluid, i.e. carrier buffer and sample solution, to a narrow liquid film contained within a channel between two parallel plates. Within the channel it is generally assumed that viscous forces maintain fluid stability. Numerous such instruments have been designed and patented for continuous flow electrophoresis.

In such continuous flow instruments the d.c. electric field is applied in a direction perpendicular to buffer and sample flow. The critical feature of such instruments seems to be the dimension of the gap between the two parallel plates, i.e., the thickness of the fluid film. This is usually of the order of 0.5 to 1.5 mm. The passage of the electric current generates heat, and thus one or both of the parallel plates are cooled. The cooling capacity of these plates sets the limit for power dissipation within the apparatus. It is implicit in such continuous flow devices, whether applied to ZE, IEF, or ITP, that separation of sample functions be obtained in a single pass through the apparatus. This requires slow flow of buffer and long residence time of the sample within the apparatus.

While such instruments are in reasonably wide use, their operation is limited by several factors. Only very dilute solutions can be utilized, of the order of 0.01 to 0.2% solute concentration, otherwise density gradients between sample and carrier buffer may cause convective disturbances. Three other factors disturb separation: (1) electroosmosis causes a parabolic flow of liquid in the plane of the electric field, electroosmosis being due to the electric charge at the inner surface of the parallel plates; (2) the downward flow of the liquid through the narrow gap also causes a parabolic flow velocity profile in a direction perpendicular to that due to electroosmosis. Thus, the residence time of the fluid in the center of the gap is much shorter than that of the fluid close to the wall; (3) finally, as the fluid at the center of the gap is warmer than at the walls, all electrophoretic parameters (conductivity, viscosity, electrical field, mobility of ions, etc.) are affected. The effects of the three factors are complex and cause the well known 'crescent phenomenon' (Strickler and Sacks, 209 Annals New York Acad. Sci. 497–514 (1973)), i.e., a crescent-like deformation of the migrating sample zones. The crescent deformation is most pronounced closest to the walls of the electrophoretic chamber. To minimize it, the sample stream is mostly injected only into the center of the gap, thus seriously limiting the throughput capacity of the apparatus. Of all these factors, gravity was assumed to be the most important limitation on the performance of the instruments. It is for this reason that McDonnell Douglas Astronautics Co. has constructed and tested is well publicized continuous flow apparatus specifically designed for operation in the reduced gravity of orbiting spacecraft.

All present instruments of the continuous flow kind were designed and are applied principally to ZE. The object of the present invention is to demonstrate how these and other difficulties with current instruments can be avoided. The invention is restricted only to IEF and ITP, where steady states are achieved, and is not applicable to ZE. Thus, the apparatus and method which are objects of the present invention may be considered as the first ones specifically designed for IEF and ITP.

SUMMARY OF THE INVENTION

The present invention is directed to a method and apparatus for separation and purification of proteins and other biological materials by isoelectric focusing (IEF) or isotachophoresis (ITP). The invention is based on the discovery that stabilization of fluid flow during preparation IEF or ITP is achievable by rapid recirculation of process fluid through the narrow channel of a continuous flow electrophoresis chamber of limited depth. Thereby are eliminated the previously enumerated causes of fluid flow disturbance due to temperature and density gradients, electroosmosis and parabolic flow.

The apparatus suitable for implementation of the invention differs from conventional continuous flow instruments in several respects: (1) there is a matched set of in- and outflow ports at the opposite end of the electrophoresis chamber; (2) means are provided for rapid recirculation of the process fluid in closed external loops between each matched set of in- and outflow ports; (3) these loops include individual refrigerated heat exchangers.

The processing method differs also in a substantial manner from the customary methods of operation of continuous flow electrophoresis chambers: (1) rather than trying to achieve the desired degree of separation in a single pass through the apparatus, only small shift towards the final steady state is achieved in every pass through the chamber; (2) rather than having slow flows and long residence times, of the order of minutes to fractions of an hour, rapid recycling is established, with residence times of the order of seconds. These and other differences in apparatus and method of operation will become obvious from further disclosure.

The stabilizing effect of rapid flow is so striking that cooling of the electrophoresis chamber is no longer necessary. In most continuous flow instruments, great emphasis is placed on uniformity of temperature within the apparatus, to avoid convective disturbances. In the present invention, the Joule heat generated by the applied electric current can be dissipated in heat exchangers external to the apparatus. This is obviously a major advantage, greatly simplifying the design of the apparatus. The Joule heat is absorbed by the latent heat capacity of the process fluid during transit through the electrophoresis chamber and released to the heat exchanger. The allowable heating within the chamber is limited only by the heat-sensitivity of the sample, rather than the stability of liquid flow.

DESCRIPTION OF THE PREFERRED EMBODIMENTS

Figure 1:
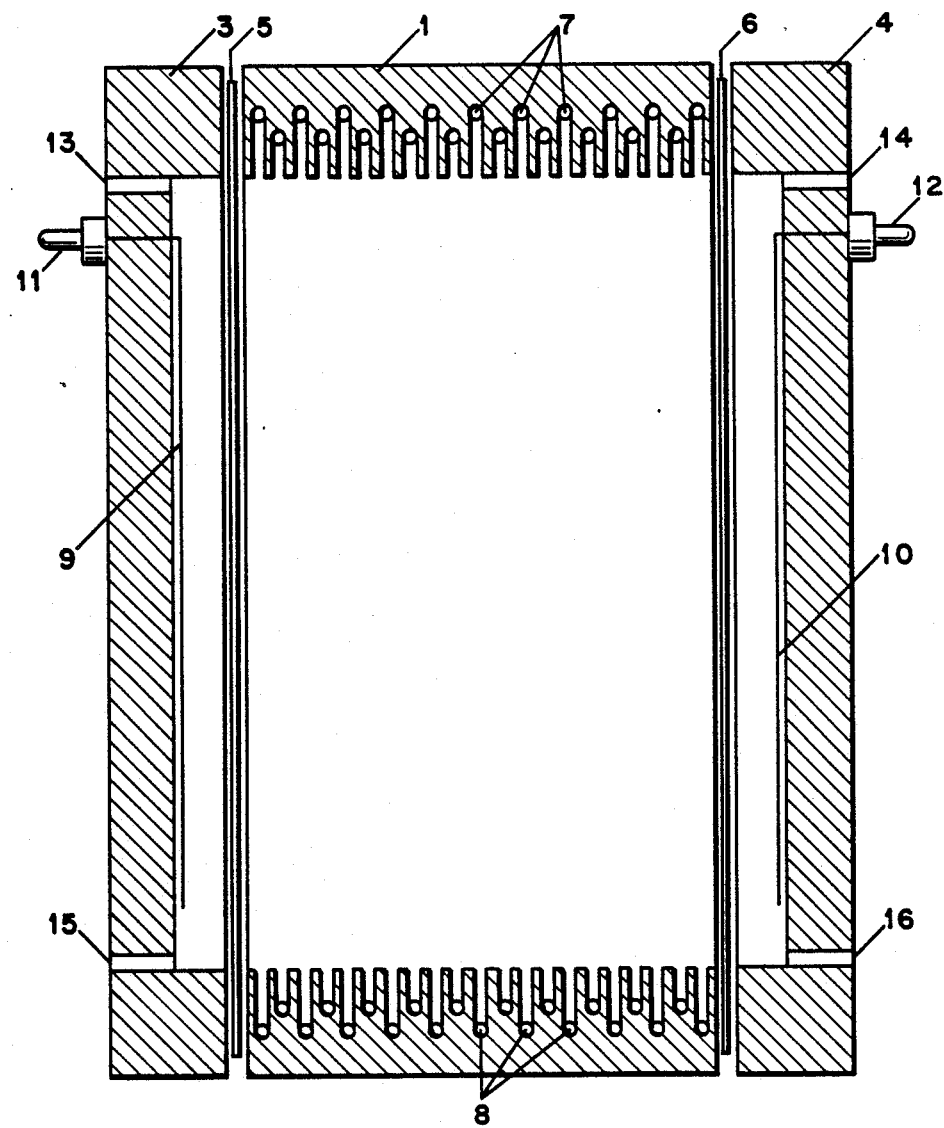
FIG. 1 is a front view of a preferred embodiment of the invention.

Before considering the apparatus embodying the invention, understanding will be facilitated by considering the principles underlying the device and method. It is an essential feature of the present invention that fluid flow disturbances inherent in continuous flow electrophoresis can be largely overcome by recirculating the fluid rapidly through the chamber, reducing the residence time to seconds only. This stabilizing effect was an unexpected and fortuitous observation during the testing of the apparatus: the faster the recirculating flow, the higher the power that can be dissipated in the apparatus before fluid instabilities are observed. The effect is very significant and not foreseeable on the basis of prior art or literature. Careful analysis of the causes has revealed that it is due to a synergistic contribution of several factors, no one of which alone suffices to produce the observed effect.

Our analysis revealed the synergistic relation between the following major factors:

1. The process is applicable only to electrophoretic methods resulting in a steady state exhibiting self-stabilizing and self-sharpening sample concentration boundaries, namely IEF and ITP. Thus, there exists the necessity of using suitable buffer mixtures: appropriate carrier ampholytes capable of generating pH gradients for IEF, and discontinuous buffer systems for ITP. Random selection of homogeneous buffers used for ZE will not result in effective fractionation.

2. To minimize gravitational effects it is necessary to maintain a short residence time of fluids within the processing chamber. Density gradients are unavoidable in all electrophoresis, but are particularly pronounced in IEF and ITP, because of the sharpness of sample concentration boundaries. Density gradients generate natural convection, but this requires a certain time element to develop. In a situation such as continuous flow electrophoresis, where both forced and natural convection can occur simultaneously, the relative importance of the buoyancy can be determined by the ratio of the Grashof and square of the Reynolds numbers:

$$\frac{Gr}{Re^2} = \frac{\text{bouyancy force}}{\text{inertia force}} = \frac{g\Delta\rho L}{\rho U^2} \quad [1]$$

here g is the gravitational acceleration, $\Delta\rho$ the density difference, L the length, and U the through-flow velocity. The convection effects will be negligible if above ratio is much smaller than 1. This requires operation at relatively high Reynolds numbers, incompatible with single pass operation and necessitating recirculation. This, in turn, is compatible only with IEF and ITP modes of operation.

3. To further minimize gravitational effects, it is helpful to orient the focused streams of flowing sample vertically, rather than horizontally. In a horizontal orientation, the denser stream of focused sample would tend to sediment in the course of transit through the chamber.

4. The most surprising discovery is the effectiveness of shear stress at the walls of the chamber to minimize electroosmosis. To the best of our knowledge, this has not been previously known, and the effect of shear stress on electroosmosis has not been investigated. Shear stress, }, is defined as the ratio of force, F, and surface, A, and is given by $$= \frac{F}{A} = -\mu \frac{dU}{dy} = -\frac{dp}{dL} y \quad [2]$$

which is the well known Newton's law of viscosity, where $\mu$ is the viscosity, U the fluid velocity at a distance y from the centerline of the channel, and p the pressure. In laminar flow through a channel between parallel plates, dp/dL is constant across the depth of the channel, as otherwise the flow would not be laminar. Thus, $\tau$ varies linearly with y, being at a maximum at the walls and zero at the center, where y=0. The total discharge, Q, per unit width, W, of the channel is given by $$\frac{Q}{W} = -\frac{dp}{dL} \frac{2b^3}{3\mu} \quad [3]$$

where b is the distance between the centerline and the wall of the channel. Substituting for dp/dL, the shear stress can be ex expressed as a function of Q/W by $$\tau = \frac{3Q}{2W} \frac{\mu}{b^3} y \quad [4]$$

Thus, while the shear stress is increasing only linearly with Q, it is proportional to the third power of 1/b. This explains the importance of keeping the channel depth to the minimum consonant with reasonable throughput and power dissipation. In practice, the wall to wall spacing of the chamber $2b=D$, of 0.05 to 0.1 cm was found best.

One may also wish to define the residence time, R, of fluid in the electric field, which is given by $$R = \frac{WLD}{Q} \quad [5]$$

which allows to define the shear stress in terms of R and D $$\tau = 12 \frac{L}{R} \frac{\mu}{D^2} y \quad [6]$$

Expressed in these terms, the shear stress is proportional to L/R and inversely proportional to the square of chamber thickness, being zero in the center of the channel and maximal at the walls. Equation 6 has some interesting implications, for instance, lengthening the chamber length L to increase throughput Q, does not result in increased shear stress, as the ratio L/R remains constant.

We are now in the position to give some typical values of one of our apparatus and its mode of operation: L=30 cm; W=6 cm, D=0.075 cm, Q=3.5 cm3/sec, U=0.01 poise (gm/cm sec) then the calculated R=3.9 sec, $\tau=168\times\gamma$(gm/cm sec2), or at $\gamma=D/2$ i.e., at the walls of the chamber, $\tau$max=6.3. Under such typical conditions, our apparatus tolerates a continuous input of 200 watts d.c. electric power without fluid disturbances. This power causes a temperature rise of approximately 12° C. in a non-refrigerated chamber, easily tolerated by most biological samples, provided the inflowing liquid was cooled in the external heat exchanger to near freezing. Optional cooling of one of the plates of the chamber avoids all temperature rise.

This should be contrasted to single pass conventional continuous flow electrophoresis instruments where residence times for IEF are usually well in excess of 600 sec, and the tolerated power is of the order of 10 watts or less.

Our apparatus differs significantly from other electrophoretic apparatus that utilizes shear for fluid stabilization. See Mattock, Aitchison and Thomson, 9 Separation and Purification Methods 1-68 (1980). That apparatus carries out separation in an annulus between two cylindrical electrodes, an inner stationary one and an outer rotating one. Sample and carrier buffer are introduced at the bottom of the annulus and the separated fractions withdrawn at the top. The apparatus can be used only for ZE and there is no possibility for fluid recycling. Moreover, liquid flows within a channel with one stationary and one moving boundary, and dU/dy rather than dp/dL is constant across the depth of the channel. Thus, the shear stress is constant across the whole channel (see equation 1).

There are significant differences in the use of shear stress for fluid stabilization in the two instruments: in the prior art apparatus, uniform shear across the channel is used; while in the present invention, shear is maximal at the wall of the chamber and zero at the channel center. This is not a trivial difference: electroosmosis is exclusively a wall effect, and that location is where maximal shear stress is needed. On the other hand, biological materials are sensitive to shear, and thus the invention offers the advantage of minimizing shear in the bulk of the liquid. Maximum flow, of course, is in the center of a channel, where in our apparatus there is zero stress. Furthermore, in the older instrument, rotationally induced shear is in a direction perpendicular to the direction of liquid flow through the annulus. In our apparatus, shear stress is in the direction of the liquid flow.

Figure 2:
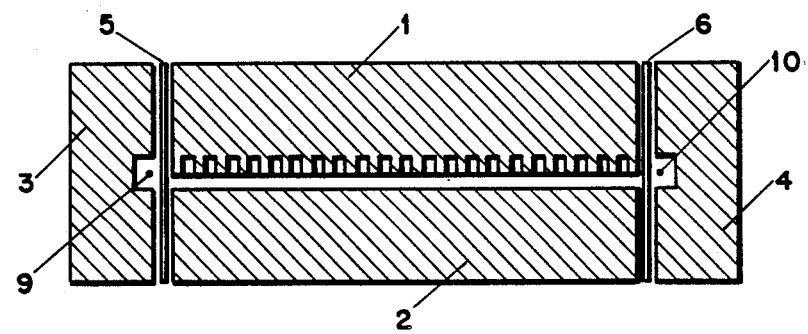
FIG. 2 is a cross-sectional top view of the chamber shown in FIG. 1, taken along plane II—II of FIG. 1.

As seen in FIGS. 1 and 2, the fluids to be processed are circulated through a processing chamber in a first direction, and exposed to a d.c. current in a second direction, roughly perpendicular to the first direction. The chamber itself is constituted by two parallel plates 1 and 2, of an electrically non-conducting material, such as plexiglass, glass, etc., these plates defining a relatively narrow channel for fluid flow. Multiple parallel entry ports 8 for process fluid are provided at one end of the chamber, matched at the opposite end of the chamber by outlet ports 7, located at the bottom and top of the chamber, respectively. Electric current is provided by electrodes 9 and 10, mounted on carriers fitted with connectors 11 and 12. The electrodes are mounted in compartments, usually lateral, of the chamber, as shown, and separated from the main cavity of the chamber by electrically conducting but protein non-permeable membranes 5 and 6. For IEF, these membranes may be either ion-permselective or electrically neutral, while only the latter are acceptable for ITP. Examples of such electrically neutral membranes are the various types of dialyzing membranes commercially available, and ion-permselective membranes may be the type used in electrodialysis. As is known in the art, the electrode chambers are provided with ports 13 and 14 for circulation of the electrolytes.

All entry and exit ports are individually connected outside of the chamber in a series of closed loops, so that a parallel and contiguous flow of individual fluid streams is established through the chamber cavity. The fact that the fluid loops outside the cavity are closed loops assures the volumetric constancy of in- and outflow through each matched set of ports. Ion transport between adjacent streams in the chamber takes place under the influence of the electric field. Separate electrolyte circulation paths are provided for each of the two electrode chambers.

For IEF, there is provided a matched number of entry and exit ports, the number depending on the number of fractions desired. ITP requires counterflow, thus necessitating inflow of buffer at one side of the chamber and outflow at the other side. This flow can be accomplished through inflow and outflow of excess fluid into the recirculation loops, at opposite sides of the chamber, or by provision for separate non-recirculating ports.

Figure 3:
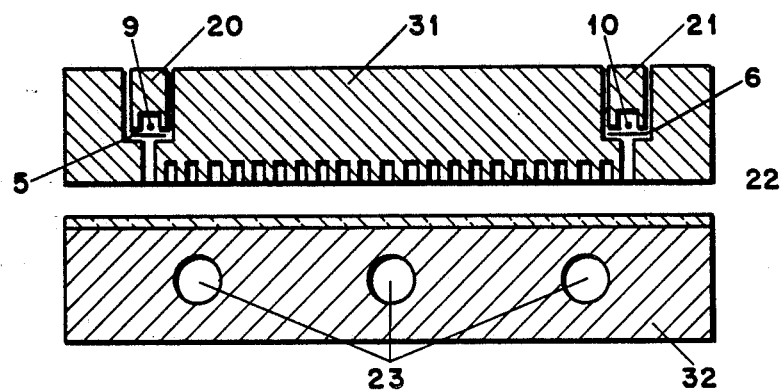
FIG. 3 is a cross-sectional top view of an alternate embodiment of the invention.

Although it has been found that the present invention eliminates the need for cooling the chamber plates, cooling means may be provided if desired, as shown in FIG. 3. Such means are most conveniently mounted on the chamber back plate, as generally it is desirable to view that chamber through a transparent covering over the front of the apparatus. Also, sealing is facilitated by mounting the electrodes in the front plate. As shown, a metallic plate 32, provided with channels 23 absorbs and transfers heat. An insulating layer 22 electrically isolates the cooling means.

Fluid addition or withdrawal during fractionation, if desired for any reason, can be effectuated through any of the external fluid channels. This is necessary for establishing counterflow in ITP, through the input of leading electrolyte at one side of the chamber and withdrawal of excess fluid so introduced at the outer side of the chamber. If desired, this input or withdrawal could also be accomplished through additional ports in the chamber.

Figure 4:
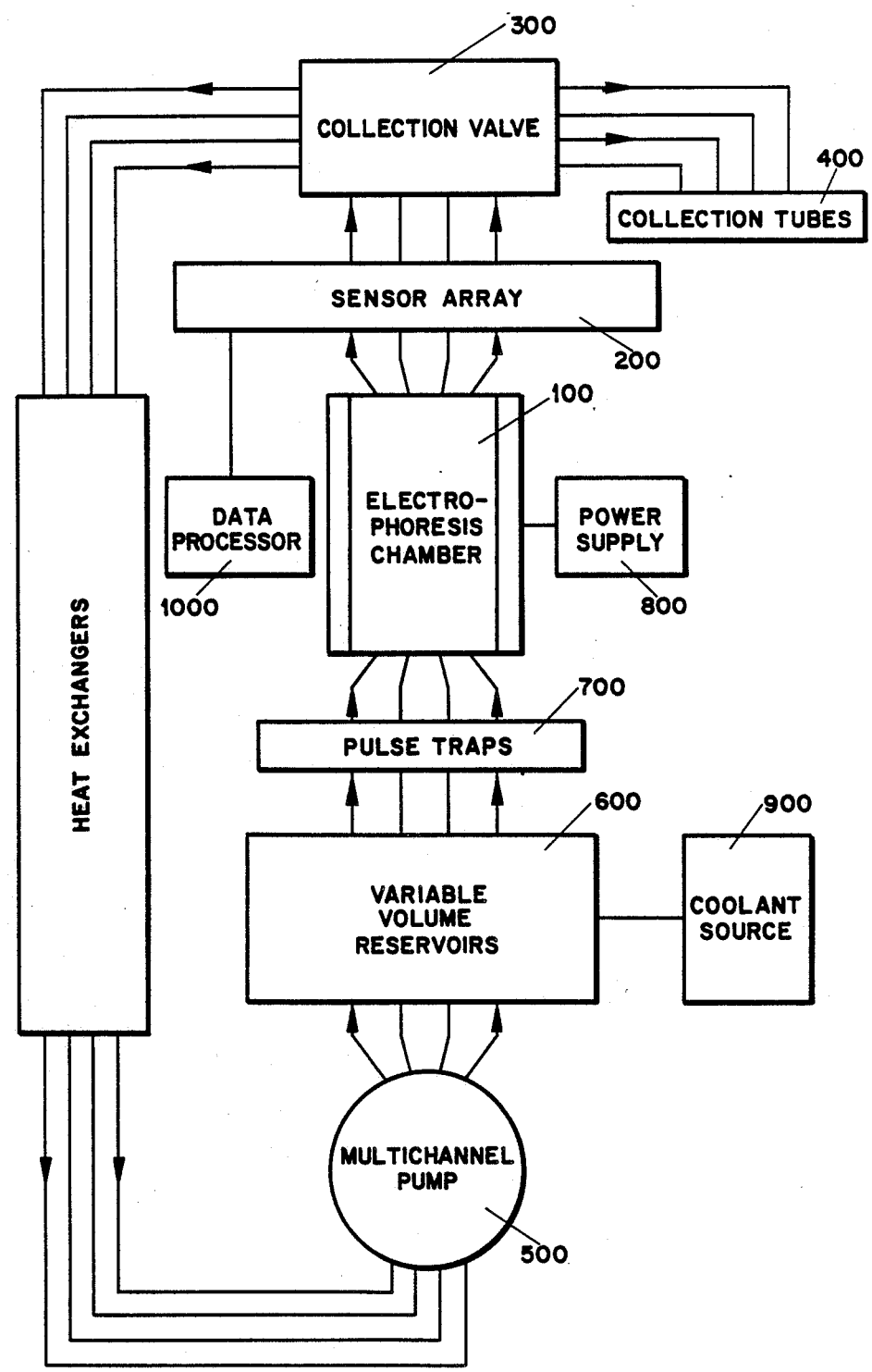
FIG. 4 is an overall schematic view of an apparatus as used for recycling IEF according to the present invention.

A system for performing IEF according to the present invention is shown in FIG. 4. There, a multichannel pump 500 provides fluid pressure in the external loops, where constancy and uniformity of flow through each channel are desirable. Preferably, the individual flows are also channeled through a heat exchanger 1100, to dissipate the Joule heat generated by the electric current. In addition, one may wish to introduce into all or some selected fluid loops sensors 200 for pH, conductivity, electric potential, optical density in the visible or ultraviolet range, temperature, or other such fluid properties.

These sensors, along with data processor 1000 and collection valve 300, comprise a monitoring means which, in addition to other detection and control purposes, can locate the position of an isotachoporetic boundary and regulate the counterflow to maintain that boundary. Finally, air and pulse traps 700, reservoirs 600 to increase the volume capacity of the system, and other attachments known to those in the art can be incorporated into the external loops.

The apparatus of FIG. 4 may be constructed of glass, a variety of machineable plastics or even ceramics. Cooling plates, if desired, can be metallic, provided they are separated from the chamber's interior by electrically insulating layers of suitable material, which could again be either glass or plastic. The front side of the of the apparatus is preferably transparent, to facilitate observation.

To initiate IEF fractionation, the apparatus is first filled with a solution containing a suitable carrier ampholyte for the establishment of the pH gradient. The sample to be fractionated can be premixed with this solution, or can be added at a later stage. The apparatus is then purged of air, which may require several reversals of flow direction through the chamber and the external circuitry. Total fluid capacity is given by the volume of the electrophoresis chamber and that of the external loops, which can incorporate variable volume expanders. As a rule, chamber volume is only a minimal faction of total volume. Circulation of suitable electrolytes is then initiated through the electrode compartments. A variety of electrolyte fluids are customarily used for this purpose, such as dilute acids or bases. Finally, recirculation of process fluid is initiated through the cooled heat exchanger and all other external accessories.

The focusing process can best be visualized using colored samples, such as red homoglobin, blue-stained albumin, or a suspension of green chloroplasts from plant leaves. At the start, a uniform colored film of flowing liquid is observed. Upon application of current, progressive focusing is seen. The pH gradient originates at the electrodes and progressively moves inwards. Thus, with a mixture of hemoglobin and blue albumin, initial clearing of color from both sides of the chamber will be seen. As the pI of the albumin is lower than that of hemoglobin, a faster blue and slower red band will be seen at the cathodic side of the chamber, the reverse being visible at the anodic side. Finally, the advancing bands of the two proteins will merge at their respective pH's in the chamber. In each pass through the chamber, the movement of the protein is imperceptible, as there is only a small shift of protein distribution in the short residence time. When final focusing is achieved, each protein will be confined to a narrow band of colored material in continous recirculation. Visually, the stability of the fluid is such that the bands appear stationary and their flow is visible only by careful observation.

The reasons for the fluid stabilization have been given in a previous section of the disclosure. Essentially, short residence time is needed to minimize gravitational effects due to density gradients, and shear stress at the walls minimizes electroosmosis. There is proportionality between shear stress and total electrical power that can be dissipated in the apparatus. This can be readily demonstrated if a colored protein sample, such as hemoglobin or a stained protein, is focused. At any electrical power, instability can be generated by lowering the flow rate, Q. This is visualized by wavering of the colored protein bands, previously sharply focused at higher power. The effect is even more dramatic if flow is completely interrupted, while maintaining full power. This results in a nearly instantaneous and dramatic disruption of the focused protein bands, this being best described as feathering of the bands in lateral directions. Rapid remixing of the contents of the electrophoresis chamber is the result. If the electric power is first stopped and then the flow interrupted, a different phenomenon is seen: the settling of the denser protein bands to the bottom of the chamber as a result of gravity. Finally, if power is stopped but recirculation maintained, there is no immediate visual effect on the colored protein bands, diffusion being quite slow.

Good results were obtained with three electrophoresis chambers, with the following internal dimensions: Chamber A: 40 matched entry and exit ports, chamber height 30 cm, width 6 cm, and variable depth (gap between front and back plate) between 0.025 and 0.15 cm. Experiments with this chamber have determined that optimal depth is of the order of 0.075 cm. Chamber B: 12 matched ports, height 20 cm, width 2.8 cm and depth 0.075 cm. Chamber C: 48 matched ports, height 30 cm, width 6 cm and depth 0.075 cm. Only chamber C had the external cooling, requiring frontal electrode compartments, as illustrated in FIG. 3.

Most experiments were run at constant power, registering also current or voltage. During focusing, the conductivity of the process fluid decreases by nearly an order of magnitude, causing an increase in applied voltage and decrease in amperage. Thus, the steady state is signaled by the constancy of these two factors. To speed up the focusing process, the power is kept at a maximum tolerated by heating and fluid stability, but it was experimentally observed that reduction of power and flow rate, once apparent steady state is reached, may marginally increase the sharpness of resolution. The reasons for this are not clear, but can probably be ascribed to increased irregularity of pump performance at high rate. The pumps employed are peristaltic pumps with planetary gear drives, to minimize wear and tear on the tubing and decrease pulsation.

Once steady state is reached, the fractions can be collected. A variety of procedures has been employed, but in any of them, the first step is to cut the power and recirculation. The fluid contained in the chamber is then drained and rejected, as it rapidly remixes. Following this, the fractions are collected by draining, pumping, or otherwise extracting the fluid from each isolated external circulation loop. Several fraction collection devices accomplishing the extraction of all channels simultaneously have been constructed, but are not object of the present invention.

Utilization of the apparatus for ITP is more complicated, as it requires the establishment of a counterflow. The chamber is filled with the leading electrolyte, as is the appropriate electrode compartment — the anodic for separation of negatively charged species and the cathodic for positively charged species. The remaining electrode is filled with the terminating electrolyte. After priming the apparatus, the leader is replaced by the terminator in a few (2–5) of the recirculating channels closest to the terminator. The sample to be separated is then injected into one or more of the circulating loops between leader and terminator and the power is applied. This injection can be in a single bolus, or can be continued for as long as it is desired during the run.

According to the principles well known to the practitioners of the art of ITP, the samples will migrate, displacing the leader, and will be followed by the terminator. At the same time, sample components will sort themselves according to their respective electrophoretic mobilities in the chosen electrolyte system. There is usually also significant concentration of sample zones, proteins often reaching a concentration of several percent. The advancing band of the fastest sample can be monitored in a variety of ways: color (if visible), absorption in the ultraviolet, conductivity, or electric potential gradient. The potential is uniform within the leader zone, but has a sharp stepwise increase at every interface between successive zones, such as leader-sample, sample-sample, or sample-terminator interface. Monitoring of potentials is as a rule most effective, because universally applicable. A colored sample is very helpful, however, for the initial setting of approximate parameters of flow and electric power.

Once the leading boundary of sample zone has sufficiently advanced, it has to be virtually immobilized by counterflow of leading electrolyte. The excess fluid so introduced has to be withdrawn from the opposite side of the chamber, occupied by the terminator. This procedure is well known to the practitioners of the art. Typically, the inflow of the leader will be carried out through the input ports close to the leader electrode and the terminator withdrawn from the ports close to the terminator electrode. Thus, quite large supplies of leader and terminator have to be available, to avoid depleting the system.

The balancing of the input flow of the leader can be adjusted either manually, to maintain constancy of the position of the leader-sample interface, or can be automated. Electronic circuitry has been constructed which senses the electric potential between each successive pair of the exit ports of the chamber, thus monitoring the whole process. When the chosen position of the critical interface is neared, counterflow is initiated. At that time the circuitry can be employed in two alternate modes: it either controls the applied power at constant leader counterflow, or adjusts the counterflow at constant power. Obviously, both have to be preset manually at approximately proper relation for the system to work effectively. Under construction is an array of sensors monitoring the ultraviolet absorption in all recirculating channels. The logic of the operation is controlled by a data processor 1000 (FIG. 4), such as a personal computer.

EXAMPLE 1

The following description summarizes a series of experiments which have been used to test the apparatus as they were being developed. All three previously described chambers were used. The objective was the isoelectric focusing separation of carbon monoxide treated human hemoglobin, a red protein, and human serum albumin, stained blue with Bromphenol Blue dye. Typically, a 1% solution (w/v) of Ampholine (Trademark of LKB Produkter, AB of Sweden), broad pH range of 3.5 to 10, was used as the carrier ampholyte, the two proteins having been used at varying concentrations, ranging from 0.2 to 5 mg/ml. The apparatus is primed with this solution and run at constant power input until separation is visually completed. "Once focusing is obtained, various combinations of pumping rates and power can be used to try to determine conditions of optimal resolution." This is easily determined visually, by observing the distribution of the colored proteins in the recirculating flow loops.

Experience has shown that the process is very forgiving, being compatible with a wide range of conditions of flow and power. Initially, there is advantage of maximizing power, to shorten the focusing time. Routinely, constant power of 200 watts was applied with residence time of liquid in the chamber of about 3–6 seconds. Before final collection, there appears to be some minor advantage in reducing the power to about 80–120 watts and prolonging the residence time to about 10 seconds.

At the end of an experiment, all the fractions are collected and analyzed for pH and protein concentration. A typical result illustrates the sharp focusing of the proteins at their respective PI values:

| tube # | pH | hemoglobin (mg/ml) | albumin (mg/ml) |
|--------|------|--------------------|-----------------|
| 10 | 7.95 | 0.11 | 0 |
| 11 | 7.78 | 0.23 | 0 |
| 12 | 7.62 | 0.71 | 0 |
| 13 | 7.47 | 2.95 | 0 |
| 14 | 7.21 | 3.25 | 0 |
| 15 | 6.99 | 0.47 | 0 |
| 16 | 6.79 | 0.20 | 0 |
| 29 | 5.09 | 0 | 0.23 |
| 30 | 4.97 | 0 | 1.38 |
| 31 | 4.84 | 0 | 3.14 |
| 32 | 4.76 | 0 | 5.78 |
| 33 | 4.69 | 0 | 6.96 |
| 34 | 4.58 | 0 | 3.18 |
| 35 | 4.48 | 0 | 0.38 |

EXAMPLE II

This example illustrates the ability to purify by isoelectric focusing monoclonal antibodies obtained from mouse ascites fluid. It also documents the ability of the apparatus to handle proteins which precipitate at their isoelectric point, a common problem. Mouse ascites fluid was diluted to ⅓ in a solution containing 1% Ampholine, pH range 5–9 and 3 molar concentration of urea. Focusing in a mode as described in Example I showed a heavy zone of precipitating proteins, which focused at about pH 4, and is of unknown origin. The antibodies were collected in 4 tubes centered around pH 7.4 and analytical isoelectric focusing in polyacrylamide gels showed that they were free of all contaminating ascites proteins. The identity of the antibodies was confirmed by radioautography using a radioactive antigen.

EXAMPLE III

This example is cited to illustrate the application of the apparatus to recycling isotachophoresis. To the best of our knowledge, this is the very first example of the establishment of an isotachophoretic system in a recycling apparatus. There was a serious question whether such a system can be established in an apparatus where the bulk of the fluid is continuously outside of the electric field.

The leading electrolyte contained 5 mM Cacodylic acid, adjusted to pH 7.4 using Tris (hydroxymethyl) aminomethane (TRIS). The terminator was 5 mM B-alanine, adjusted to pH 9.2 with barium hydroxide. The sample was a mixture of hemoglobin and albumin, 250 mg each, added with an appropriate spacer, i.e. 500 mg of the dipeptide Gly-Gly. Processing revealed a very sharp recirculating leading zone of albumin, separated from that of hemoglobin by a colorless zone of Gly-Gly. The zone was virtually immobilized by applying counterflow of the leading electrolyte. As in all experiments, collection of separated proteins zones was accomplished by stopping the recirculation and the applied power and collecting the contents of all the recirculation loops.

We claim:

1. A process for isoelectric focusing or isotachophoresis of fluids, comprising the steps of:
    establishing a fluid flow within a chamber comprised of a top end with a plurality of parallel closely spaced ports, a bottom end with a plurality of parallel, closely spaced ports, said top and bottom ends being substantially parallel to each other, with the top end's and bottom end's ports being closely matched, a front wall and a rear wall, said walls being electrically non-conducting, substantially parallel to each other and separated by a distance of between about 0.025 and about 0.25 cm, and two side plates, said plates carrying electrodes
    applying an electrical potential across said fluid flow in a direction substantially transverse to said fluid flow;
    recycling the fluid between each of said top and bottom matched ports through external loop means
    cooling the fluid while in said external loop means; and
    maintaining the residence time of the fluid within said chamber at a value less than 90 seconds.

2. The process of claim 1, wherein said maintaining step maintains said residence time at a value between 1 and 20 seconds.

3. The process of claim 1, wherein said recycling step includes the step of adding or withdrawing fluid from said external loop means.

4. The process of claim 1, further comprising the steps of:
    monitoring the position of an isotachophoretic boundary; and
    regulating counterflow to control the position of said boundary.

5. The process of claim 1, further comprising the steps of cooling at least one portion of said chamber with wall cooling means.

6. The process of claim 1, wherein said maintaining step maintains said residence time of the fluid within said chamber at a value less than 20 seconds.

7. Apparatus for isoelectric focusing or isotachophoresis of fluids, comprising:
    a chamber, including
    an input end with a plurality of parallel entry port means therein,
    an output end with a plurality of parallel exit port means therein;

a front wall and a rear wall, said walls being substantially mutually parallel, electrically non-conducting, and are separated by a distance between about 0.025 and 0.25 cm, and two substantially mutually parallel lateral plates, said plates carrying electrodes;

fluid flow means for establishing fluid flow in a direction from said entry port means to said exit port means, including external fluid loop means for recycling the fluid externally of said chamber, in fluid communication with said chamber through said entry port and said exit port means;

pump means for establishing fluid pressure within said chamber and said external loop means; and heat exchange means for extracting heat from the fluid flowing within said external loop means;

collector means for collecting separated sample fractions from said external loop means;

said fluid flow means being capable of totally exchanging the fluid in said chamber in less than 90 seconds; and means for applying an electric potential across said chamber in a direction substantially transverse to said direction of fluid flow.

8. The apparatus of claim 7, wherein each one of said plurality of entry port means is aligned in matched spatial relation with one of said plurality of exit port means, such that said fluid flow within said chamber occurs between related pairs of said entry port means and exit port means; and said external loop means includes separate loop means for providing fluid communication between each said related pair of entry port means and exit port means.

9. The apparatus of claim 8, wherein said fluid flow means are capable of totally exchanging the fluid in said chamber in less than 20 seconds.

10. The apparatus of claim 8, wherein said external loop means further include sensor means for monitoring selected properties of the fluid.

11. The apparatus of claim 8, wherein said external loop means further include reservoir means for controlling the capacity of the apparatus.

12. The apparatus of claim 8, wherein said external loop means further include means for adding or withdrawing fluid from the apparatus.

13. The apparatus of claim 8, wherein at least one of said front or rear walls includes cooling means for controlling the temperature of same.

14. The apparatus of claim 8, further comprising monitoring means for locating the position of an isotachophoretic boundary and regulating counterflow to maintain the position of same.

15. A method for isoelectric focusing or isotachophoresis of fluids, comprising the steps of:

establishing a fluid flow in a first direction within a chamber including opposed, substantially parallel walls to contain said fluid flow within the chamber, each of the walls extending in a plane within is parallel to said fluid flow;

spacing said substantially parallel, opposed walls relative to one another by a distance of between about 0.025 and about 0.25 cm;

applying an electrical potential across the fluid flow within said chamber in a second direction which is substantially transverse to said first direction;

recycling fluids in said fluid flow through a multichannel external loop coupled to said chamber;

cooling the fluid flow in said multichannel external loop; and maintaining the fluid flow to limit the residence time of the fluids within said chamber to less than about 90 seconds.

16. An apparatus for isoelectric focusing or isotachophoresis of fluids, which comprises:

a chamber having a plurality of inlet ports and a plurality of associated outlet ports opposing said inlet ports;

the chamber including a pair of opposed, substantially parallel walls extending between said inlet ports and said outlet ports to contain a fluid flow through the chamber from the inlet ports to the outlet ports;

said oppposed walls being spaced from one another by a distance of between about 0.025 and about 0.25 cm;

a plurality of recirculation loops, each coupling one of the outlet ports to an associated one of the inlet ports to recycle the fluid flow through the chamber;

a multichannel pump for recirculating the fluid flow through the chamber and the recirculation loops;

means for applying an electrical potential transversely across the fluid flow within the chamber;

a heat exchanger for cooling the fluid flow within the recirculation loops; and the multichannel pump operating to totally exchange fluids o the fluid flow within the chamber in less than about 90 seconds.

17. The apparatus of claim 16, wherein said opposed walls are spaced from one another by a distance of between about 0.05 and about 0.1 cm.

* * * * *